United States Patent [19]

Green

[11] 4,391,281

[45] Jul. 5, 1983

[54] ULTRASONIC TRANSDUCER SYSTEM AND METHOD

[75] Inventor: Philip S. Green, Atherton, Calif.

[73] Assignee: SRI International, Menlo Park, Calif.

[21] Appl. No.: 757,132

[22] Filed: Jan. 6, 1977

[51] Int. Cl.³ .............................................. A61B 10/00
[52] U.S. Cl. ...................................... 128/660; 73/644
[58] Field of Search ............... 128/2 V, 24 A, 2.05 Z, 128/660; 73/67.5 R, 67.7, 621, 642, 67.85, 644; 340/8 L

[56] References Cited

U.S. PATENT DOCUMENTS

| | | | |
|---|---|---|---|
| 3,168,659 | 2/1965 | Bayre et al. | 73/67.5 R |
| 3,251,219 | 5/1966 | Hertz et al. | 128/2 V X |
| 3,270,274 | 2/1966 | Green | 340/8 L |
| 3,387,604 | 6/1968 | Erikson | 128/24 A |
| 3,687,219 | 8/1972 | Longlois | 73/644 X |
| 3,818,898 | 6/1974 | Williams | 128/2 V |
| 3,927,557 | 12/1975 | Viertl | 73/67.5 R |
| 3,958,559 | 5/1976 | Glenn et al. | 73/67.5 R X |
| 4,001,766 | 1/1977 | Hurwitz | 340/8 L |

FOREIGN PATENT DOCUMENTS

| | | | |
|---|---|---|---|
| 2414777 | 10/1975 | Fed. Rep. of Germany | 128/2 V |
| 2318420 | 7/1975 | France | 128/2 V |
| 260815 | 5/1970 | U.S.S.R. | 128/2 V |

OTHER PUBLICATIONS

Knollman, G. C. et al., "Variable-Focus Liquid-Filled Hydroacoustic Lens", Jrnl. of Acoustic Soc. of Amer., V49, No. 1, pt. 2, pp. 253-255.
Halliday & Resnick, "Physics", Ch. 41, Reflection & Refraction, Wiley & Sons, New York, 1967, pp. 1020-1023.
Hertz, C. H., "Vts Engrg in Heart Diagnosis", Amer. Jrnl. Cardiology, V. 19, Jan. 1967, pp. 6-17.
Lemons et al., "Acoustic Microscopy; Biomed Applications", Science, vol. 188, No. 4191, pp. 905-911, May 1975.
McDicken, W. N. et al., "An UTS Instrument for Rapid B-scanning of the Heart", Ultrasonics, V. 12, No. 6, Nov. 1974, pp. 269-272.
Ray, C. D., "Textbook of Medical Engineering", Yearbook Publishers, Chicago, 1974, p. 1058.
Handbook of Chemistry & Physics, CRC publisher, 1964, p. E-28.

*Primary Examiner*—Lee S. Cohen
*Assistant Examiner*—Francis J. Jaworski
*Attorney, Agent, or Firm*—Victor R. Beckman

[57] ABSTRACT

An ultrasonic transducer system for use with tissue is shown, which system includes a container of liquid acoustic coupling medium within which focused transducer means are located. Focusing of the transducer means may be effected acoustically, as by use of an acoustic lens, and/or electronically, as by use of a transducer array. The liquid medium container is closed at one end by a rigid acoustically transparent window, or diaphragm, for acoustically coupling to the skin and underlying tissue of the subject under investigation. The material of the liquid acoustic coupling medium is selected so that the velocity of propagation of acoustic waves therein is substantially less than the velocity of the acoustic waves within the tissue under investigation. By using a low speed-of-sound coupling medium a shorter propagation path may be employed than is required by prior art transducer arrangements in which the speed-of-sound in the tissue and coupling fluid is substantially the same. Operation in either scanning or non-scanning modes is contemplated, and scanning, when employed, may be effected mechanically or electronically. In the sector scanning mode, the system may be operated in a manner such that the angular sector swept out by the focused beam in the tissue exceeds that in the low speed-of-sound liquid coupling medium as a result of refraction at the window interfaces.

13 Claims, 5 Drawing Figures

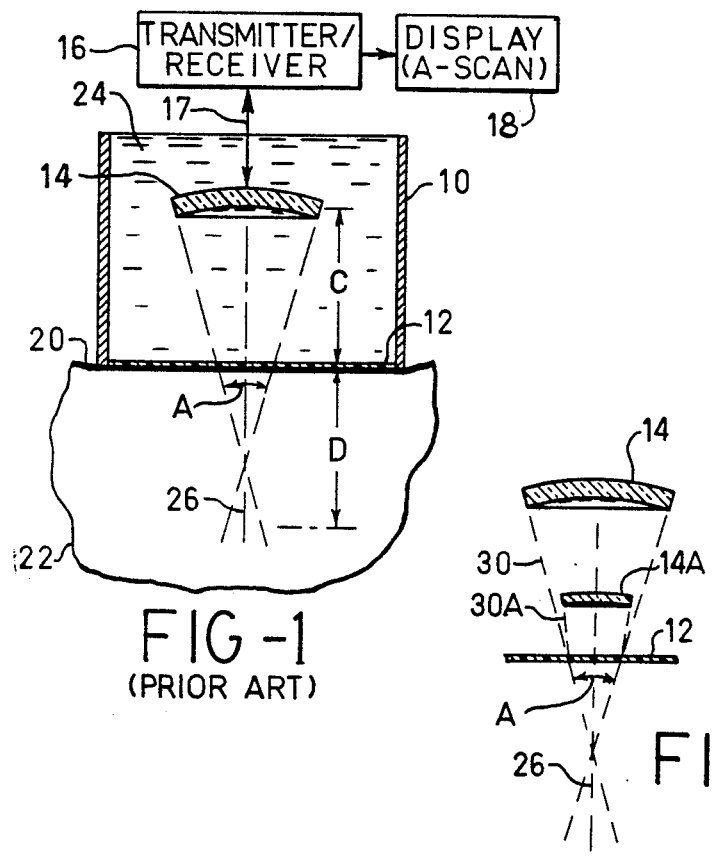
FIG-1 (PRIOR ART)
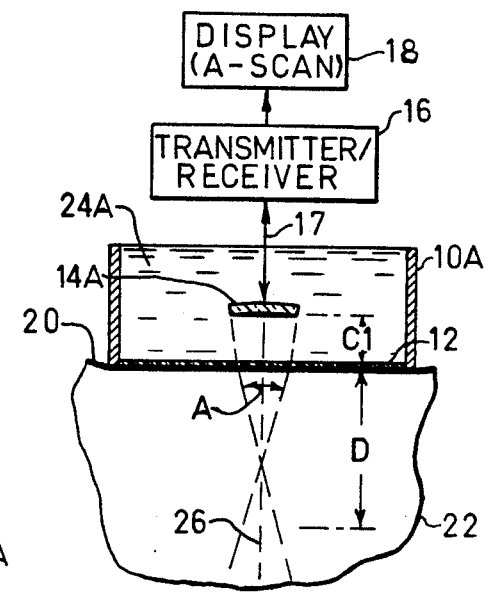
FIG-2
FIG-3
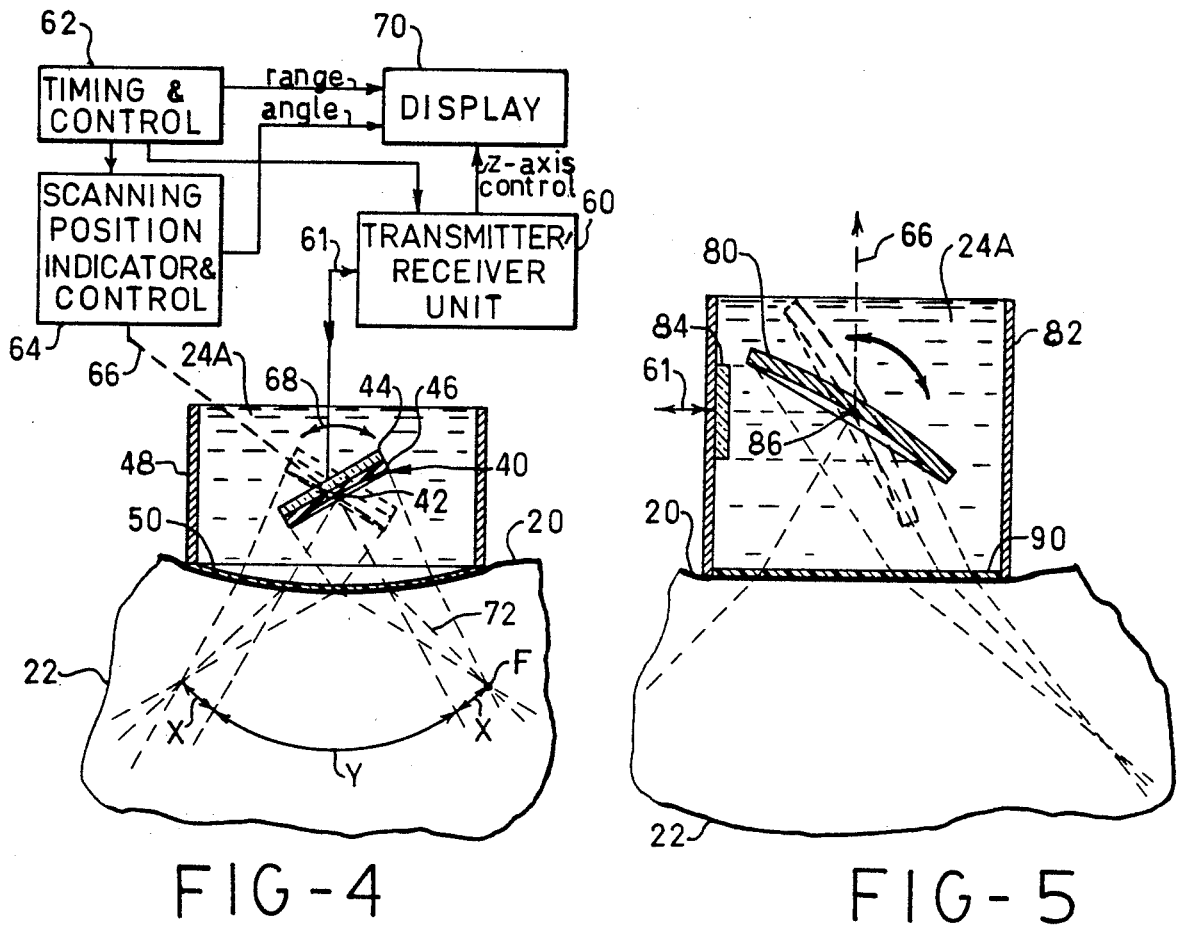
FIG-4
FIG-5

ULTRASONIC TRANSDUCER SYSTEM AND METHOD

ORIGIN OF INVENTION

The invention described herein was made in the course of a contract with the Department of Health, Education and Welfare.

BACKGROUND OF INVENTION

Various ultrasonic methods currently are employed in diagnostic investigations of living tissue. One such widely used method is the sonar-like A-scan method wherein short ultrasonic pulses from an ultrasonic transducer coupled to the patient's skin are projected into the tissue. Reflections from tissue interfaces received by the transducer are detected and the resultant electrical signal may be displayed at the screen of a cathode ray tube. Since the round trip travel time of the reflected pulse is related to the distance from the transducer to the reflecting layer, the presentation of these waves at the cathode ray tube permits the operator to directly measure such distances.

The well-known B-scan method is similar to the above-described A-scan method in that both methods employ a narrow-beam transducer to project short ultrasonic pulses into the tissue and to detect pulses reflected from tissue interfaces. However, with B-scan, a two-dimensional image is produced by scanning the ultrasonic beam, either electronically or mechanically, across the area of interest. A cathode ray tube display may be provided in which one of the orthogonal deflection voltages is proportional to the transducer position and the other to the time elapsed since the last pulse was transmitted. The reflected ultrasonic pulse is used to intensity modulate the display.

Often, the transducer means employed with such A and B-scan systems is located within a container of acoustic transmission liquid, which container has a liquid tight acoustically transparent window therein for acoustically coupling to the skin of the subject under investigation. A coupling liquid such as water, within which the velocity of propagation of acoustic waves is substantially the same as in the tissue, often is employed. Refractive displacement of acoustic waves travelling across the window interfaces is minimized by use of a thin window. A fluid path length within the water equal to or greater than the greatest imaging depth within the tissue is required to prevent multiple reflections between the transducer and transducer window from being superimposed upon the image display.

SUMMARY OF THE INVENTION AND OBJECTS

An object of this invention is the provision of ultrasonic transducer means of the "non-contact" type for use in medical ultrasonic systems of the pulse operating type in which the fluid path length between the transducer and acoustically transparent window in the container for the transducer means required to prevent multiple reflections therebetween from interfering with the display of echo signals is substantially less than with prior art non-contact type transducer means.

An object of this invention is the provision of sector scanning type ultrasonic transducer method and means for use in ultrasonic imaging of tissue in which the angular sweep of the focused beam is magnified in passing from within the transducer housing to underlying tissue under investigation.

The above and other objects and advantages of this invention are achieved by a housing which is closed at one end by a rigid acoustically transparent diaphragm, or window, and which housing is filled with a coupling liquid for the support of a focused ultrasonic beam from a pulse-operated focusing transducer contained in the coupling liquid. The window is engaged with the skin of the subject for acoustically coupling the focusing transducer and subject. A coupling liquid with a low sonic propagation velocity is employed. In particular, a coupling liquid having a sonic propagation velocity which is, say, 50 percent lower than the velocity of ultrasound within the tissue is employed. With the use of such low sonic propagation velocity liquid in the system, the acoustic path between the transducer and diaphragm may be made substantially shorter than with prior art arrangements of similar type without the superimposition on the display of signals produced as a result of the multiple reflection of acoustic signals between the transducer and diaphragm.

A better understanding of the invention, and objects and advantages thereof, may be obtained from the following description taken in conjunction with the accompanying drawings. In the drawings, wherein like reference characters refer to the same parts in the several views:

FIGS. 1 and 2 are combination block diagram and cross-sectional views showing a prior art ultrasonic A-scan system and a novel A-scan system which embodies this invention, respectively, FIG. 3 is a diagrammatic view which combines portions of the FIG. 1 and FIG. 2 showings for use in illustrating benefits and advantages of the transducer system of this invention over similar prior art arrangements, FIG. 4 is a combination block diagram and cross-sectional view showing a B-scan ultrasonic imaging system which also embodies this invention, and FIG. 5 is a simplified cross-sectional view of a modified form of transducer system embodying this invention, which system includes an oscillatory acoustic reflector for sector scanning purposes.

Reference first is made to FIG. 1 wherein a prior art non-contact type transducer system is shown comprising a container, or housing, 10 closed at one end by an acoustically transparent window 12. Focusing transducer means 14 disposed within the housing are supplied with high frequency energy pulses from the transmitter section of a pulsed transmitter/receiver unit 16 over line 17 for the recurrent transmission of short focused ultrasonic pulses through acoustic transmission coupling liquid 24, diaphragm 12, and the skin 20 of the subject for pulse insonification of the underlying tissue 22 along the acoustic axis 26. After a time delay following transmission of the last pulse, the receiver portion of the transmitter/receiver unit 16 is enabled for processing of echo signals received by the focused transducer 14 from discontinuities within the tissue 22 along the acoustic axis. Since the round-trip travel time of the reflected pulse is related to the distance from the transducer to the reflecting layer, a convenient cathode ray tube display is provided at display unit 18 wherein one of the orthogonal deflection signals is proportional to the amplitude of the reflected ultrasonic pulse and the other is proportional to the time elapsed since the last pulse was transmitted.

In prior art non-contact type transducer systems, such as shown in FIG. 1, the housing 10 is filled with a liquid acoustic transmission coupling medium 24 selected such that the acoustic waves have a velocity of propagation therein which substantially equals the velocity of propagation in the tissue 22. Water (within which acoustic waves propagate at a velocity of approximately 1480 meters per second as compared to a velocity of approximately 1538 meters per second in tissue) often is used as the coupling medium. (From the above, it will be apparent that the term "tissue" as employed herein refers to soft tissue, as distinguished from bone and similar connective tissue in which the propagation velocity is substantially greater than 1538 meters per second.) With substantially equal sonic propagation velocity materials at opposite faces of the diaphragm 12, the sonic waves enter and exit the diaphragm along substantially parallel paths since refraction at the inner and outer interfaces of the diaphragm is substantially equal. Also, thin diaphragms often are used to minimize refraction effects.

As is well understood, in prior art A-scan systems such as illustrated in FIG. 1 the acoustic path length within the acoustic coupling liquid 24 inside the container must equal, or exceed, the maximum tissue depth to be examined to prevent multiple reflections between the transducer 14 and diaphragm 12 from being superimposed on the visual display provided at the cathode ray tube. For example, in the illustrated non-contact type transducer system, wherein the transducer 14 is located a distance C from the diaphragm, operation to substantially the depth D within the tissue 22 is possible without interference with multiple reflection echo signals, where the distance D substantially equals the distance C. (As is apparent, the same limitations concerning acoustic path lengths apply also to prior art pulsed B-scan imaging systems.)

A novel pulsed A-scan ultrasonic system embodying this invention is shown in FIG. 2, to which Figure reference now is made. The system may include the same pulsed transmitter/receiver unit 16 and display 18 shown in the prior art arrangement of FIG. 1. In FIG. 2, the transducer system is shown comprising a container 10A closed at one end by a rigid diaphragm 12, focusing transducer means 14A disposed within the container 10A, and acoustic transmission coupling liquid 24A within the container 10A for acoustically coupling the transducer means 14A and diaphragm 12. The transducer means 14A are connected through line 17 to the pulse-echo transmitter/receiver unit 16 for pulse energization of the transducer and processing of echo signals in a conventional manner such as described above with reference to the FIG. 1 arrangement.

In accordance with the present invention, a coupling liquid 24A having a sonic propagation velocity which is substantially lower than the sonic propagation velocity within the tissue 22, is employed. Although the ratio of the sonic propagation velocity within the coupling liquid to the sonic propagation velocity within the tissue is not critical, a velocity ratio on the order of 1-to-2, or greater, is desirable to realize substantial benefits from the invention. Slow speed-of-sound coupling liquids which may be employed in this invention include, for example, Freons, other fluorinated hydrocarbons, and the like. The commercially available fluorinated hydrocarbons of the family named Fluorinet by the manufacturer, Minnesota Mining and Manufacturing Company, are particularly useful. In particular the fluorinated hydrocarbon FC75, in which ultrasound propagates at a velocity of approximately 600 meters per second is particularly well adapted for use in this invention. With a sonic propagation of approximately 1500 meters per second in the tissue, a velocity ratio of approximately 1:2.5 is provided by the use of FC75 as the liquid coupling medium.

A comparison of FIGS. 1 and 2, and an examination of FIG. 3, provide visual indication of advantages of this invention. In the diagram of FIG. 3 both of the transducer means 14 and 14A are shown so as to provide a direct comparison of the FIG. 1 and FIG. 2 arrangements. Obviously, FIG. 3 does not disclose an operating system but simply is included for purposes of illustration and comparison. Firstly, it will be noted that the use of a low velocity of propagation coupling liquid 24A for coupling the transducer and diaphragm enables the use of a shorter acoustic path length in such liquid without interference caused by multiple reflections therebetween; the path lengths within the coupling fluids being identified by the reference characters C and C1 in FIGS. 1 and 2, respectively. With a sonic propagation velocity ratio of 2.5 to 1 in the case of water versus FC75, it will be apparent that the travel time between the transducer means and diaphragm is the same in both the FIG. 1 and FIG. 2 arrangements despite a 2.5 to 1 difference in the acoustic path lengths C and C1.

Secondly, not only may the transducer 14A be located nearer the diaphragm, but a smaller size transducer may be employed to provide the transducer system with the same effective aperture angle as the prior art arrangement of FIG. 1. As seen in the drawings, the same aperture angle A is shown within the tissue 22 for both the FIG. 1 and FIG. 2 transducer systems. The reduction in size of the transducer 14A results both from its location nearer the diaphragm and from the different refraction of ultrasonic waves at opposite interfaces of the diaphragm when a coupling liquid 24A having a different index of refraction from that of the tissue 22 is used. This is best illustrated in the diagram of FIG. 3 wherein the transducers 14 and 14A are shown located in the same positions relative to the diaphragm as shown in FIGS. 1 and 2. In FIG. 3 it will be seen that the transducer 14A is located within the cone 30 of focus of ultrasonic waves from the transducer 14. Ultrasonic waves 30A from the transducer 14A are directed, or bent, inwardly toward the acoustic axis 26 as a result of refraction at the diaphragm interfaces when the slow velocity of propagation fluid 24A is used, to provide for the same aperture angle A within the tissue as provided in the FIG. 1 prior art arrangement. Such smaller-size transducer 14A is more easily fabricated than the larger transducer 14. Also, the additional focusing effect provided by refraction at the diaphragm reduces the curvature of the transducer 14A required to produce the necessary focusing action. Other advantages are realized with transducer systems employing different focusing means. For example, where a focusing lens is used to provide the necessary focusing action, as shown, in FIG. 4, a thinner lens may be used, as will become apparent hereinbelow.

Reference now is made to FIG. 4 wherein a novel beam scanning transducer system which embodies this invention is illustrated. There, a focusing transducer 40 is shown which is mounted for pivotal movement about a pivot axis 42 extending in a direction normal to the plane of the drawing. For purposes of illustration, the focusing transducer 40 is of the lens type, comprising a piezoelectric body 44 with suitable electrodes disposed thereon at opposite faces thereof, and an acoustic focusing lens 46 attached to one face thereof. Such lens-type focusing transducer means are well known and require no detailed description.

The focusing transducer means 40 are disposed within a container, or housing, 48 which is closed at one end by a diaphragm 50. Low speed-of-sound coupling liquid 24A, such as FC75, is used to acoustically couple the transducer means 40 to the diaphragm 50. The diaphragm, in turn, engages the subject's skin 20 for acoustically coupling to the underlying tissue 22. In FIG. 4, for purposes of illustration only and not by way of limitation, a curved rigid diaphragm 50 is shown comprising a section of a sphere. The radius of curvature of the semispherical diaphragm is greater than the distance to the diaphragm from the pivot axis 42 of the transducer for bending of the acoustic beam axis at the diaphragm when passing non-radially therethrough. As a result, the angular sector swept out by the focused beam in the tissue 22 exceeds that in the coupling liquid 24A. In FIG. 4 the angular sector Y identifies that sector which would be swept out in the tissue 22 if coupling liquid such as water was employed, as in prior art arrangements. With the use of a slow speed-of-sound coupling liquid, such as FC75, in the transducer housing, refraction at the diaphragm interfaces provides an increase in the angular sweep within the tissue which sweep, as measured from the diaphragm, is increased by angular amounts X at opposite ends of the scan.

The novel transducer system of FIG. 4 may be employed with an otherwise-conventional B-scan arrangement which, for purposes of illustration, is shown comprising a transmitter/receiver unit 60 under control of a timing and control unit 62 for the recurrent generation of high frequency energy pulses which are supplied over line 61 to the transducer means 40. Focused ultrasonic wave pulses from the transducer means 40 pass through the low speed-of-sound coupling liquid 24A, diaphragm 50, and the patient's skin 20 for pulse insonification of the underlying tissue 22. Echo signals received by the focusing transducer means 40 from discontinuities within the region of the ultrasonic beam are converted to electrical signals which are supplied to the receiver section of the transmitter/receiver unit 60. The B-scan receiver, which also is under control of the timing and control unit 62, is gated on after a delay period following generation of the last B-scan pulse for receiving echo signals from within a range of depths along the beam axis 72 about the beam focal point F within the tissue 22.

A scanning position indicator and control unit 64, connected to the transducer 40 through mechanical linkage 66, serves to periodically rock, or oscillate, the transducer about its pivot axis 42 in the direction of the arrow 68 for sector scanning to provide for a two-dimensional display, at a display unit 70. A sweep angle signal related to the transducer position along its scanning arc is provided to the display unit 70 under control of the scanning position indicator and control unit 64, which sweep angle signal is adjusted for the increased angular sweep of the focused beam within the tissue 22 provided by the novel transducer system. A range deflection signal related to the time elapsed from the last transmitted pulse is supplied to the display from the timing and control unit 62. The B-scan receiver output, from unit 60, is connected as a Z-axis signal for the display unit 70 for intensity modulation of the cathode ray tube beam in accordance with the amplitude of the receiver output signal for a real time ppi (plane position indicator) type display.

It will be apparent that an arcuate section within the tissue lying in the plane of the drawing along the acoustic axis 72 of the transducer system is imaged by the B-scan system. Since the angular sector (Y+X+X) swept out by the focused beam within the tissue 22 exceeds that in the low speed-of-sound coupling liquid 24A, it will be apparent that a smaller mechanical sector oscillation is required for a given sector sweep. Additionally, as illustrated above, because of the shorter wavelength in the coupling fluid 24A, a transducer of smaller area is required. As a result, the inertia thereof is reduced, which is of particular benefit in mechanically scanned systems of the type illustrated. Also, the transducer lens 46 may be made thinner, (as compared to the thickness required in the case of the use of water as a coupling liquid), thereby further reducing the inertia of the focusing transducer. The use of a thinner lens also reduces the effect on the image of multiple reverberations in the lens. In addition, since a shorter acoustical path length through the coupling liquid 24A within the housing 48 is required, a more compact transducer system is possible.

Beam focusing is not limited to the curved transducer body type, illustrated in FIGS. 1-3, or to the lens focusing type illustrated in FIG. 4. In FIG. 5, to which reference now is made, focusing is provided by use of a curved acoustic reflector 80 within a container 82 filled with a slow speed-of-sound coupling liquid 24A, such as FC75. A non-focusing type transducer 84 is shown mounted at one wall of the container for the generation and/or reception of ultrasonic waves. The acoustic reflector 80 (as was the transducer 40 of FIG. 4) is mounted for pivotal movement about a pivot axis 86. The remainder of the ultrasonic imaging system, i.e. the transmitter/receiver, scanning position indicator and control, and display units (not shown) may be of the same type illustrated in FIG. 4 and described above. Obviously, the mechanical linkage 66 from the scanning position indicator and control unit is attached to the reflector 80 in the FIG. 5 arrangement for sector scanning, rather than to a transducer. For purposes of illustration, a plane rigid diaphragm 90 is shown for coupling the transducer system to the tissue. It will be seen that, again, the angular sector swept out by the focused beam from the reflector 80 within the tissue 22 exceeds that within the coupling fluid 24A to provide the arrangement with many of the same relative advantages as that of the FIG. 4 arrangement including the use of a smaller sized transducer and reflector, and shorter propagation path within the coupling liquid as compared to a similar arrangement employing water, or the like, as a coupling liquid.

The invention having been described in detail in accordance with the requirements of the Patent Statutes, various other changes and modifications will suggest themselves to those skilled in this art. For example, the invention may employ an electronically focused and/or scanning transducer array rather than acoustically focused transducers. Also, the diaphragm 50 of the FIG. 4 arrangement may be formed with a lower radius of curvature than the distance from the diaphragm to the center of rotation 42 of the transducer, in which case the sector scan within the coupling liquid 24A may be converted to a substantially rectilinear scan within the tissue 22. In addition, the diaphragm surfaces may be suitably shaped, e.g. as a thin meniscus lens, to correct for aberrations which may otherwise result. Also, in the arrangement of FIG. 5, a focusing transducer may be employed together with an oscillatory reflector to provide for the desired focused sector scanning ultrasonic beam. A pulser, gated signal source, chirped signal source, or the like, may be included in the transmitter for pulse energization of the transducer means. The invention also may be employed with continuous wave (CW) signal arrangements in addition to the illustrated pulsed transmitter/receiver systems. Additionally, arrangements employing separate transmitter and receiver transducers are contemplated. It is intended that the above and other such changes and modifications shall fall within the spirit and scope of the invention as defined in the appended claims.

I claim:

1. A medical ultrasonic system for the non-invasive examination of a soft tissue region within a subject's body comprising, focusing transducer means, a container for said focusing transducer means having a liquid tight acoustically transparent rigid diaphragm for acoustically coupling directly to the subject's skin, sonic coupling liquid within the container for acoustically coupling the focusing transducer means to said diaphragm, pulse operated transmitter/receiver means connected to said transducer means for energization of said transducer means for producing ultrasonic waves which are coupled to the subject's skin through said coupling liquid and diaphragm and for processing electrical signals produced by said transducer means upon receipt of ultrasonic waves reflected from discontinuities within the tissue of the subject, and indicating means for the display of echo signals received from discontinuities within the subject's body, the material of said coupling liquid being selected so that the velocity of propagation of acoustic waves therein is substantially less than the velocity of propagation of acoustic waves in said soft tissue, the acoustic path between the transducer means and diaphragm being substantially less than the maximum distance in soft tissue within the subject's body from which echo signals are received and displayed without interference by display of multiple reflections from the diaphragm.

2. A medical ultrasonic system as defined in claim 1 for A-scan display of reflected ultrasonic waves at said indicating means.

3. A medical ultrasonic system for the non-invasive examination of a soft tissue region within a subject's body comprising, focusing transducer means, a container for said focusing transducer means having a liquid tight acoustically transparent rigid diaphragm for acoustically coupling directly to the subject's skin, sonic coupling liquid within the container for acoustically coupling the focusing transducer means to said diaphragm, pulse operated transmitter/receiver means connected to said transducer means for energization of said transducer means for producing ultrasonic waves which are coupled to the subject's skin through said coupling liquid and diaphragm and for processing electrical signals produced by said transducer means upon receipt of ultrasonic waves reflected from discontinuities within the tissue of the subject, indicating means coupled to said transducer means for B-scan display of reflected ultrasonic waves received from a soft tissue region within the subject's body, the material of said coupling liquid being selected so that the velocity of propagation of acoustic waves therein is substantially less than the velocity of propagation of acoustic waves in said soft tissue, the acoustic path between the transducer means and diaphragm being substantially less than the maximum distance in soft tissue within the subject's body from which echo signals are received and displayed without interference by display of multiple reflection from the diaphragm, and means for pivotally oscillating said focusing transducer means within said container for sector scanning thereof, the ultrasonic beam axis being bent outwardly at said rigid diaphragm adjacent opposite ends of the scan whereby the angular sector swept out by the beam in the soft tissue region for B-scan display exceeds the angular sector swept out by the beam within the coupling liquid.

4. A medical ultrasonic system for the non-invasive examination of a soft tissue region within a subject's body comprising, focusing transducer means, a container for said focusing transducer means having a liquid tight acoustically transparent rigid diaphragm for acoustically coupling directly to the subject's skin, sonic coupling liquid within the container for acoustically coupling the focusing transducer means to said diaphragm, pulse operated transmitter/receiver means connected to said transducer means for energization of said transducer means for producing ultrasonic wave pulses which are coupled to the subject's skin through said coupling liquid and diaphragm and for processing electrical signals produced by said transducer means upon receipt of ultrasonic waves reflected from discontinuities within the tissue of the subject, the material of said coupling liquid being selected so that the velocity of propagation of acoustic waves therein is substantially less than the velocity of propagation of acoustic waves in said soft tissue, said focusing transducer means comprising a piezoelectric body for the generation of non-focused ultrasonic wave pulses, and a curved ultrasonic reflector disposed in the path of said wave pulses for focusing the same, said reflector being movable about a pivot axis, and means for pivoting said reflector about said pivot axis for sector scanning of said focused beam.

5. In a method of examining soft tissue of a subject by the use of pulsed ultrasonic waves comprising, recurrently energizing focusing ultrasonic transducer means located within a container of low sonic speed coupling fluid, as compared to the sonic speed in said soft tissue, to produce recurrent ultrasonic wave pulses, directing said ultrasonic wave pulses through an acoustically transparent rigid diaphragm in engagement with the subject's skin for pulse insonification of underlying soft tissue, receiving at said focusing ultrasonic transducer means ultrasonic waves reflected from discontinuities within the soft tissue and converting the same to electrical signals which are supplied to a receiver, and supplying the receiver output to display means for the display of echo signals including those received from soft tissue discontinuities at a depth substantially greater than the ultrasonic beam path length between said transducer means and diaphragm without superimposition on the display of multiple reflections between the diaphragm and transducer means.

6. In a method of examining soft tissue by use of pulsed ultrasonic waves comprising, recurrently energizing focusing ultrasonic transducer means located within a container of low sonic speed coupling fluid, as compared to the sonic speed in said soft tissue, to produce recurrent ultrasonic wave pulses, directing said ultrasonic wave pulses through an acoustically transparent rigid diaphragm in engagement with the subject's skin for pulse insonification of underlying soft tissue, receiving at said focusing ultrasonic transducer means ultrasonic waves reflected from discontinuities within the soft tissue and converting the same to electrical signals which are supplied to a receiver, supplying the receiver output to display means for the display of echo signals including those received from soft tissue discontinuities at a depth substantially greater than the ultrasonic beam path length between said transducer means and diaphragm without superimposition on the display of multiple reflections between the diaphragm and transducer means, and sector scanning the ultrasonic wave pulses produced by said focusing ultrasonic transducer such that the angular sweep of the ultrasonic wave pulses within said soft tissue exceeds that within the low sonic speed coupling fluid.

7. In a method of examining soft tissue as defined in claim 6 wherein said ultrasonic transducer means are located within a container of coupling fluid having a velocity of propagation of acoustic waves which is less than one half that of the velocity of propagation of acoustic waves within the soft tissue of the subject.

8. A medical ultrasonic system for the non-invasive examination of a soft tissue region within a subject's body comprising, focusing transducer means comprising a piezoelectric body formed with opposite faces having electrodes disposed thereon, one face of which piezoelectric body is concavely curved for focusing, a container for said focusing transducer means having a liquid tight acoustically transparent rigid diaphragm for acoustically coupling directly to the subject's skin, sonic coupling liquid within the container for acoustically coupling the focusing transducer means to said diaphragm, pulse operated transmitter/receiver means connected to said transducer means for producing ultrasonic waves which are coupled to the subject's skin through said coupling liquid and diaphragm and for processing electrical signals produced by said transducer means upon receipt of ultrasonic waves reflected from discontinuities within the tissue of the subject, the material of said coupling liquid being selected so that the velocity of propagation of acoustic waves therein is substantially less than the velocity of propagation of acoustic waves in said soft tissue, indicating means coupled to said transducer means for B-scan display of echo signals received from discontinuities within the subject's body, and means for pivotally oscillating said focusing transducer means within said container for sector scanning thereof, the ultrasonic beam axis being bent outwardly at said rigid diaphragm adjacent opposite ends of the scan whereby the angular sector swept out by the beam in the soft tissue region for B-scan display exceeds the angular sector swept out by the beam within the coupling liquid.

9. A medical ultrasonic system for the non-invasive examination of a soft tissue region within a subject's body comprising, focusing transducer means comprising a piezoelectric body with electrodes disposed at opposite body faces and an acoustic lens attached to one face of the body for acoustic wave focusing, a container for said focusing tranducer means having a liquid tight acoustically transparent rigid diaphragm for acoustically coupling directly to the subject's skin, sonic coupling liquid within the container for acoustically coupling the focusing transducer means to said diaphragm, pulse operated transmitter/receiver means connected to said transducer means for energization of said transducer means for producing ultrasonic waves which are coupled to the subject's skin through said coupling liquid and diaphragm and for processing electrical signals produced by said transducer means upon receipt of ultrasonic waves reflected from discontinuities within the tissue of the subject, the material of said coupling liquid being selected so that the velocity of propagation of acoustic waves therein is substantially less than the velocity of propagation of acoustic waves in said soft tissue, indicating means coupled to said transducer means for B-scan display of echo signals received from discontinuities within the subject's body, and means for pivotally oscillating said focusing transducer means within said container for sector scanning thereof, the ultrasonic beam axis being bent outwardly at said rigid diaphragm adjacent opposite ends of the scan whereby the angular sector swept out by the beam in the soft tissue region for B-scan display exceeds the angular sector swept by the beam within the coupling liquid.

10. In a medical ultrasonic system for the non-invasive examination of a soft tissue region within a subject's body, the combination comprising, focusing transducer means for producing a focused ultrasonic beam, a container for said focusing transducer means having a liquid tight acoustically transparent rigid diaphragm for acoustically coupling directly to the subject's skin, sonic coupling liquid within the container for acoustically coupling the focusing transducer means to said diaphragm, the material of said coupling liquid being selected so that the velocity of propagation of acoustic waves therein is substantially less than the velocity of propagation of acoustic waves in said soft tissue, and means for angularly scanning the focused ultrasonic beam across the rigid diaphragm whereby the angular sweep of the focused beam within the soft tissue region exceeds the angular sweep of the beam inside the container as the beam sweeps the rigid diaphragm.

11. In a medical ultrasonic system as defined in claim 10 wherein said means for angularly scanning the focused ultrasonic beam includes mechanical scanning means.

12. In a method of examining soft tissue of a subject by use of focused ultrasonic waves the steps comprising, energizing focusing ultrasonic transducer means located within a container of low sonic speed coupling fluid, as compared to the sonic speed in said soft tissue, to produce ultrasonic waves, directing focused ultrasonic waves from said focusing ultrasonic transducer means through an acoustically transparent rigid diaphragm in engagement with the subject's skin for insonification of underlying soft tissue, and angularly scanning focused ultrasonic waves directed through said rigid diaphragm whereby the angular sweep of the ultrasonic waves within the soft tissue exceeds the annular sweep thereof inside the container during scanning of the rigid diaphragm.

13. In a method of examining soft tissue as defined in claim 12 which includes the use of mechanical scanning means for angularly scanning focused ultrasonic waves.

* * * * *